United States Patent
Nita et al.

(12) 
(10) Patent No.: US 6,942,620 B2
(45) Date of Patent: Sep. 13, 2005

(54) CONNECTOR FOR SECURING ULTRASOUND CATHETER TO TRANSDUCER

(75) Inventors: Henry Nita, Redwood Shores, CA (US); Martinos Tran, Tracy, CA (US)

(73) Assignee: Flowcardia Inc, Sunnyvale, CA (US)

( * ) Notice: Subject to any disclaimer, the term of this patent is extended or adjusted under 35 U.S.C. 154(b) by 143 days.

(21) Appl. No.: 10/666,459

(22) Filed: Sep. 19, 2003

(65) Prior Publication Data

US 2004/0059227 A1 Mar. 25, 2004

Related U.S. Application Data

(63) Continuation-in-part of application No. 10/251,227, filed on Sep. 20, 2002, now Pat. No. 6,702,748.

(51) Int. Cl.$^7$ ................................................. A61B 8/14
(52) U.S. Cl. ...................................................... 600/459
(58) Field of Search ................................ 600/437–472; 604/19–22, 96; 606/78, 167, 169, 180

(56) References Cited

U.S. PATENT DOCUMENTS

| | | | | |
|---|---|---|---|---|
| 4,665,906 A | * | 5/1987 | Jervis | .......................... 606/78 |
| 5,100,423 A | * | 3/1992 | Fearnot | ....................... 606/159 |
| 5,324,255 A | * | 6/1994 | Passafaro et al. | ............. 604/22 |
| 5,326,342 A | * | 7/1994 | Pflueger et al. | ............... 604/22 |
| 5,342,292 A | * | 8/1994 | Nita et al. | ..................... 604/22 |
| 5,417,672 A | | 5/1995 | Nita et al. | |
| 6,702,748 B1 | * | 3/2004 | Nita et al. | .................. 600/459 |

* cited by examiner

*Primary Examiner*—Ali Imam
(74) *Attorney, Agent, or Firm*—Raymond Sun (57) ABSTRACT

An ultrasound system has an ultrasound transducer having a transducer housing and a horn provided at the distal end of the transducer housing, an ultrasound transmission member, a sonic connector that is connected to the horn and the proximal end of the ultrasound transmission member, and a catheter knob having a proximal end that is coupled to the distal end of the transducer housing. The catheter knob has a proximal bore that houses the sonic connector. The system also includes a nesting piece that is retained inside the proximal bore of the catheter knob. The nesting piece can be moved from a first position where the sonic connector is received inside the nesting piece to a second position where the sonic connector is separated from the nesting piece when ultrasound energy is being propagated through the ultrasound transmission member.

20 Claims, 7 Drawing Sheets

CONNECTOR FOR SECURING ULTRASOUND CATHETER TO TRANSDUCER

RELATED CASES

This is a continuation-in-part of Ser. No. 10/251,227, filed Sep. 20, 2002, now U.S. Pat. No. 6,702,748 entitled "Connector for Securing Ultrasound Catheter Transducer", the entire disclosure of which is incorporated by this reference as though set forth fully herein.

BACKGROUND OF THE INVENTION

1. Field of the Invention

The present invention pertains to medical equipment, and more particularly, to a device and method for attaching an ultrasound catheter to an ultrasound transducer which prevents frequency shifts and minimizes the mechanical impact of the handling connection area during a medical procedure.

2. Description of the Prior Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, require the use of relatively small diameter ultrasound catheters which are sufficiently small and flexible to undergo transluminal advancement through the tortuous vasculature of the aortic arch and coronary tree. These ultrasound catheters incorporate a very small diameter ultrasound transmission member which extends through such catheters. The proximal end of the ultrasound transmission member is typically connected to an ultrasound transducer via a sonic connector.

The attachment of the ultrasound transmission member to an ultrasound transducer plays a very important role in ultrasound energy propagation. The attachment region needs to be accurately aligned and free of mechanical stress and other interfaces. For example, undesirable stress at the attachment region can be caused by pressing upon, pushing, pulling, torquing, bending or bumping the attachment region during use of the ultrasound catheter. In addition, it is preferable for the sonic connector to be free from any interface (i.e., contact) with any other component during energy transmission. Otherwise, such stresses and interfaces can negatively impact the propagation of ultrasound energy through the ultrasound transmission member. Contact of the sonic connector with any other part of the catheter housing during the delivery of ultrasound energy might also cause a shift in frequency and impact performance.

Thus, there still exists a need for an improved connection of the proximal end of the ultrasound transmission member to an ultrasound transducer.

SUMMARY OF THE DISCLOSURE

It is an object of the present invention to provide an improved connection between the ultrasound catheter and the ultrasound transducer.

It is yet another object of the present invention to improve the propagation of ultrasound energy by limiting and minimizing the impact of undesirable external forces.

In order to accomplish the objects of the present invention, there is provided an ultrasound system and method of using the ultrasound system during a medical procedure. The ultrasound system has an ultrasound transducer having a transducer housing and a horn provided at the distal end of the transducer housing, an ultrasound transmission member, a sonic connector that is connected to the horn and the proximal end of the ultrasound transmission member, and a catheter knob having a proximal end that is coupled to the distal end of the transducer housing. The catheter knob has a proximal bore that houses the sonic connector. The system also includes a nesting piece that is retained inside the proximal bore of the catheter knob. The nesting piece can be moved from a first position where the sonic connector is received inside the nesting piece to a second position where the sonic connector is separated from the nesting piece when ultrasound energy is being propagated through the ultrasound transmission member.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
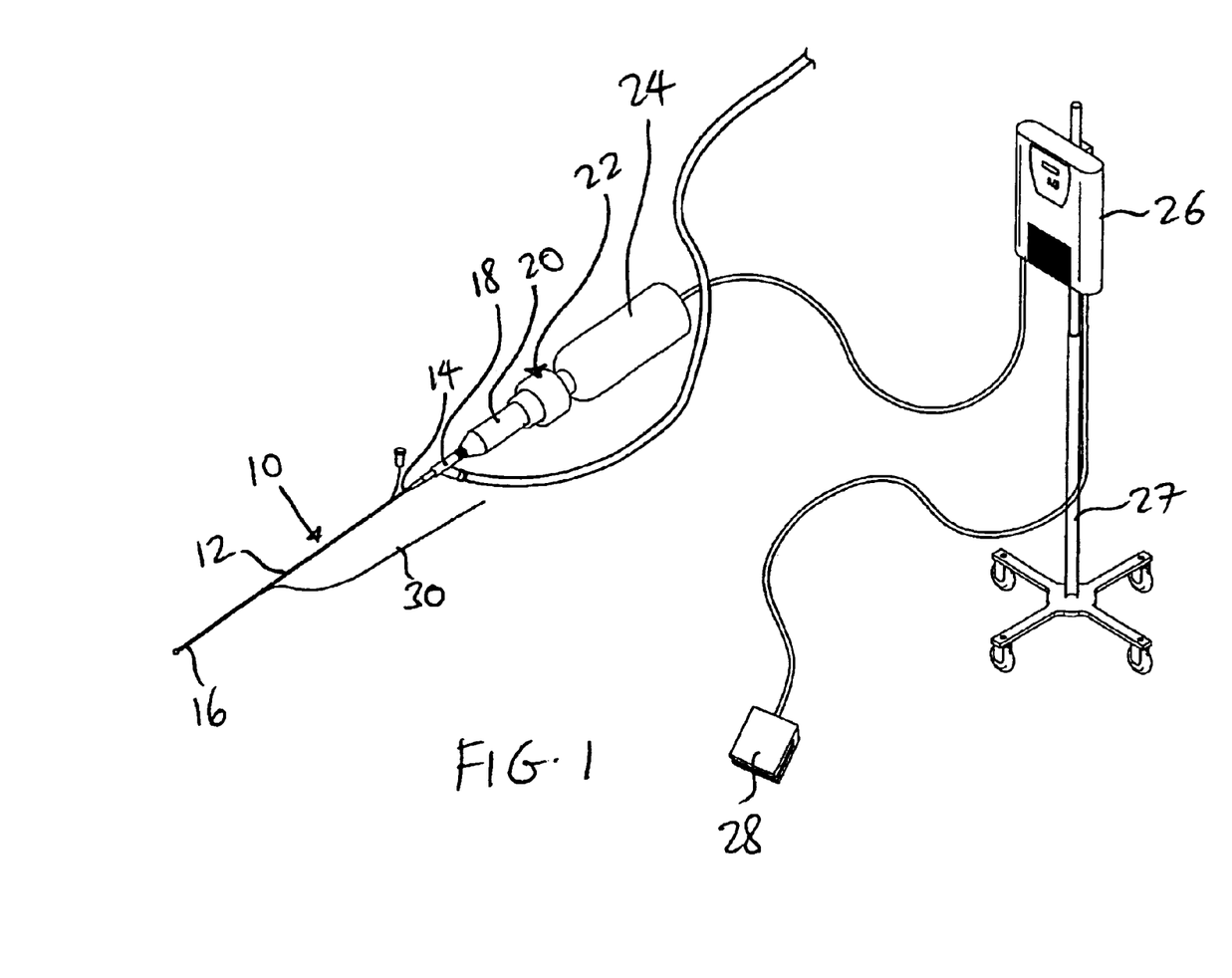
FIG. 1 is a perspective view of an ultrasound system according to one embodiment of the present invention.
Figure 3:
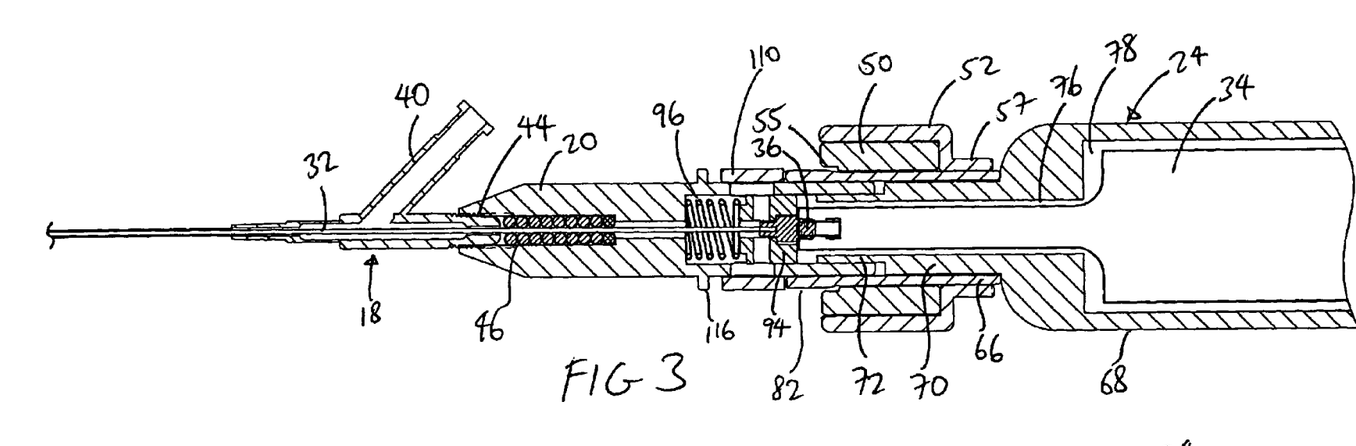
FIG. 3 is a cross-sectional view of the Y-connector, the catheter knob, the slide collar assembly and the transducer housing of the system of FIG. 1 with the slide collar assembly in the non-supporting position.
Figure 4:
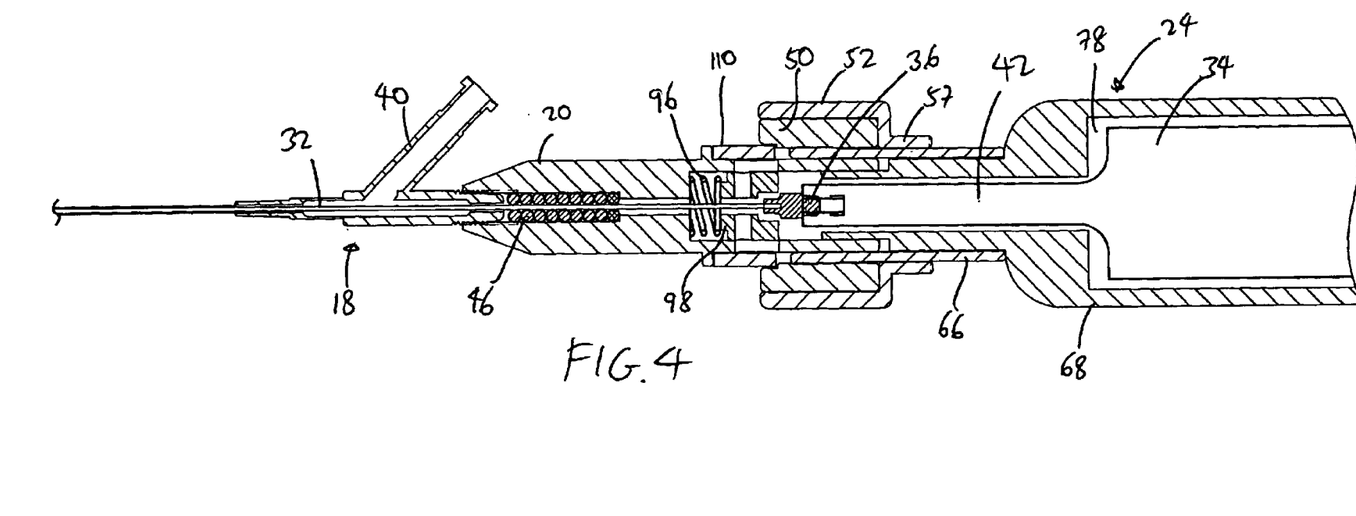
FIG. 4 is a cross-sectional view of the Y-connector, the catheter knob, the slide collar assembly and the transducer housing of the system of FIG. 1 with the slide collar assembly in the supporting position.

FIG. 1 illustrates an ultrasound system according to the present invention for use in ablating and removing occlusive material inside the vessel of an animal or human being. The ultrasound system includes an ultrasonic catheter device 10 which has an elongate catheter body 12 having a proximal end 14, a distal end 16, and defining at least one lumen extending longitudinally therethrough. The ultrasound catheter device 10 is operatively coupled at its proximal end 14, by way of a Y-connector 18, a catheter knob 20, and a slide collar assembly 22, to an ultrasound transducer housing 24. As shown in FIGS. 3–4, an ultrasound transducer 34 is housed inside the transducer housing 24. The ultrasound transducer 34 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 34, which converts the electrical signal to ultrasound energy. Such ultrasound energy subsequently passes through the catheter device 10 and is delivered to the distal end 16.

Figure 2:
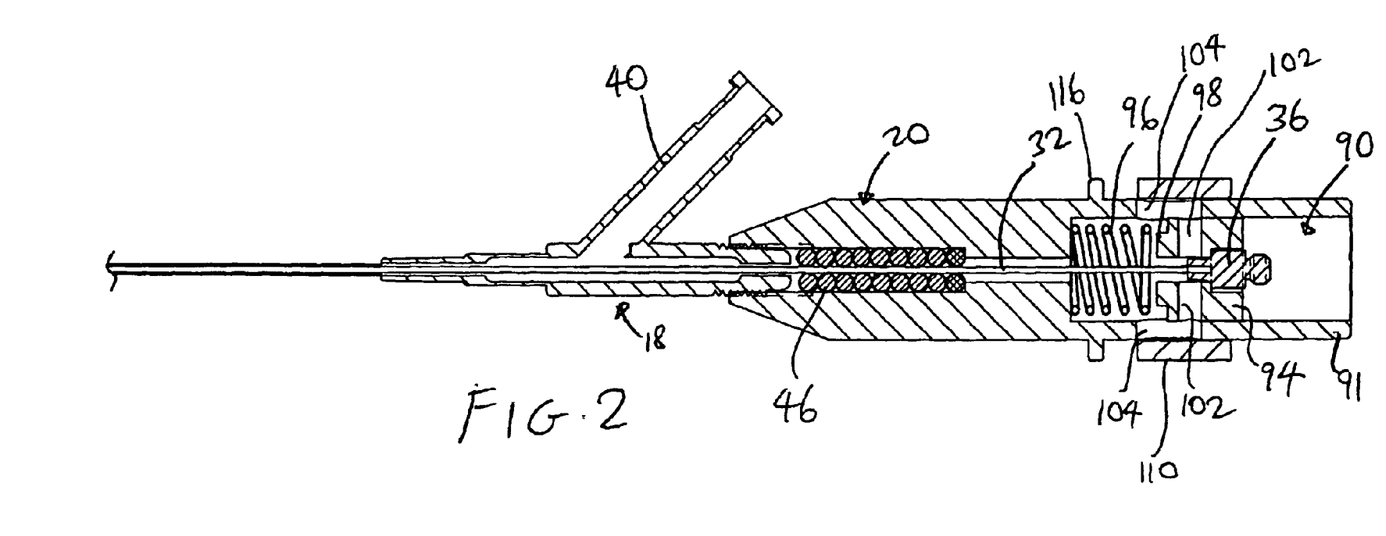
FIG. 2 is a cross-sectional view of the Y-connector and catheter knob of the system of FIG. 1.

Referring also to FIGS. 2–4, an ultrasound transmission member 32 extends through the lumen of the catheter 10 from the distal end 16 to the proximal end 14. The ultrasound transducer 34 is coupled via a sonic connector 36 (described in greater detail below) to the ultrasound transmission member 32, so that the ultrasound energy can be passed through the sonic connector 36 and the ultrasound transmission member 32 to be delivered to the distal end 16 of the catheter 10. A guidewire 30, which can be any conventional monorail or over-the-wire guidewire, may be utilized in conjunction with the catheter 10 in a manner that is well-known in the catheter art.

The frontal portion of the Y-connector 18 is connected to the proximal end 12 of the catheter 10 using techniques that are well-known in the catheter art. An injection pump (not shown) or IV bag (not shown) can be connected, by way of an infusion tube (not shown), to an infusion port or sidearm 40 of the Y-connector 18. The injection pump can be used to infuse coolant fluid (e.g., 0.9% NaCl solution) into and/or through the lumen of the catheter 10. Such flow of coolant fluid may be utilized to prevent overheating of the ultrasound transmission member 32 extending longitudinally through the lumen of the catheter 10. Such flow of the coolant fluid through the lumen of the catheter 10 serves to bathe the outer surface of the ultrasound transmission member 32, thereby providing for an equilibration of temperature between the coolant fluid and the ultrasound transmission member 32. Thus, the temperature and/or flow rate of coolant fluid may be adjusted to provide adequate cooling and/or other temperature control of the ultrasound transmission member 32. In addition to the foregoing, the injection pump may be utilized to infuse a radiographic contrast medium into the catheter 10 for purposes of imaging. Examples of iodinated radiographic contrast media which may be selectively infused into the catheter 10 via the injection pump are commercially available as Angiovist 370 from Berlex Labs, Wayne, N.J. and Hexabrix from Malinkrodt, St. Louis, Mo.

The proximal end of the ultrasound transmission member 32 is attached to the sonic connector 36 which is configured to effect operative and removable attachment of the proximal end of the ultrasound transmission member 32 to the distal horn 42 of the ultrasound transducer 34. The sonic connector 36 is preferably configured and constructed to permit passage of ultrasound energy through the ultrasound transmission member 32 with minimal lateral side-to-side movement of the ultrasound transmission member 32 while, at the same time, permitting unrestricted longitudinal forward/backward vibration or movement of the ultrasound transmission member 32.

The ultrasound transmission member 32 may be formed of any material capable of effectively transmitting the ultrasonic energy from the ultrasound transducer 34 to the distal end 16 of the catheter 10, including but not necessarily limited to metal, plastic, hard rubber, ceramic, fiber optics, crystal, polymers, and/or composites thereof. In accordance with one aspect of the invention, all or a portion of the ultrasound transmission member 32 may be formed of one or more materials which exhibit super-elasticity. Such materials should preferably exhibit super-elasticity consistently within the range of temperatures normally encountered by the ultrasound transmission member 32 during operation of the catheter 10. Specifically, all or part of the ultrasound transmission member 32 may be formed of one or more metal alloys known as "shape memory alloys". Such superelastic metal alloys are well-known in the art and will not be described in any further detail herein.

The proximal end of the Y-connector 18 is attached to the distal end of the catheter knob 20 by threadably engaging the proximal end of the Y-connector 18 inside a threaded distal bore 44 at the distal end of the catheter knob 20. O-rings 46 are provided in the threaded distal bore 44 to minimize transverse vibrations. The proximal end of the catheter knob 20 receives the extension 70 of the transducer housing 24 and is supported by the slide collar assembly 22. The slide collar assembly 22 is positioned over the distal end of the transducer housing 24, and has a non-supporting position where the slide collar assembly 22 is retracted towards the transducer housing 24, and has a supporting position where the slide collar assembly 22 is extended to cover at least a portion of the catheter knob 20. Thus, the slide collar assembly 22 functions as a support member that is disposed on the transducer housing 24 to support at least a portion of the catheter knob 20.

Figure 5:
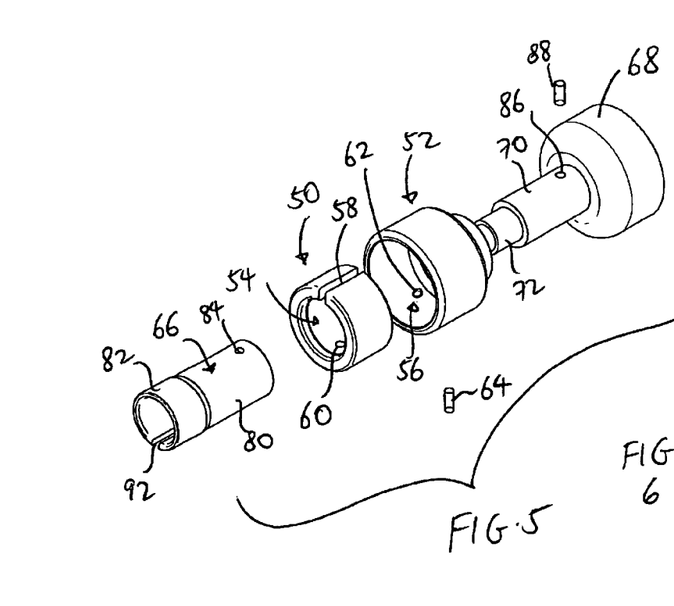
FIG. 5 is an exploded perspective view of some of the elements of the slide collar assembly of the system of FIG. 1.
Figure 6:
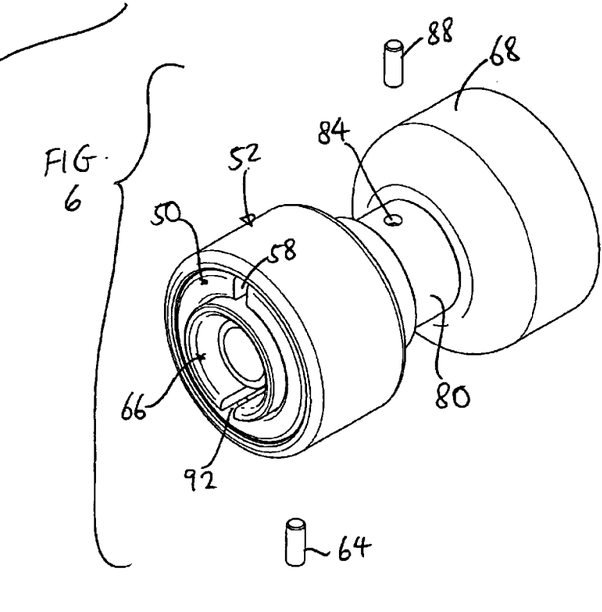
FIG. 6 is an assembled perspective view of the elements of FIG. 5.

Referring also to FIGS. 5 and 6, the slide collar assembly 22 has an inner ring 50 (also referred to as collar 50) and an outer ring 52 (also referred to as collar 52). The inner ring 50 has a bore 54 and a longitidunal slit 58 that extends through the length of the inner ring 50. The distal portion of the bore 54 can be stepped as shown at 55 (see FIG. 3) to function as a pushing surface that pushes a nesting piece 94 (described below) in a distal direction as the inner ring 50 is moved from the non-supporting position to the supporting position. The outer ring 52 also has a bore 56, and has a narrowed proximal end 57. The inner ring 50 is retained inside the bore 56 of the outer ring 52 and abuts the narrowed proximal end 57 which acts as a stop to limit the proximal movement of the inner ring 50. Each of the inner ring 50 and the outer ring 52 has an opening 60 and 62, respectively, that are aligned with each other and that are adapted to receive a locking pin 64. A tubular inner sleeve 66 extends through the inside of the bore 54 of the inner ring 50 to ensleeve the first extension 70 of the transducer housing 24, as explained below. The sleeve 66 has a proximal section 80 and an enlarged distal section 82. The inner ring 50 is normally fitted around the proximal section 80 when the slide collar assembly 22 is in the non-supporting position, but the inner ring 50 is fitted around the distal section 82 when the slide collar assembly 22 is in the supporting position. Thus, providing the distal section 82 in an enlarged configuration allows for the inner ring 50 to achieve a friction-fit with the distal section 82, while the inner ring 50 experiences a loose fit over the proximal section 80.

The transducer housing 24 has a cylindrical wall 68 having a distal extension that comprises two stepped cylindrical extensions 70 and 72 extending from the distal end of the cylindrical wall 68. The first extension 70 is attached to the distal end of the cylindrical wall 68, and has a greater outer diameter than the second extension 72 that is attached to the distal end of the first extension 70. A throughbore 76 extends from the hollow interior 78 of the cylindrical wall 68 and through the extensions 70 and 72. The throughbore 76 can have the same diameter throughout its length. The second extension 72 is adapted to be received inside the proximal bore 90 of the catheter knob 20, while the first extension 70 is received inside the sleeve 66. In addition, an opening 84 is provided in the proximal section 80 of the sleeve 66 and is aligned with a corresponding opening 86 on the first extension 70, with the openings 84, 86 adapted to receive a locking pin 88 that secures the sleeve 66 to the first extension 70 at a fixed position.

A longitudinal slot 92 is provided on the sleeve 66. When the slide collar assembly 22 is in the non-supporting position (i.e., inner ring 50 positioned over the proximal section 80), the slot 92 is opened. However, when the slide collar assembly 22 is moved to the supporting position, the inner ring 50 is positioned over the distal section 82 and compresses the enlarged distal section 82 to close the slot 92. With the slot 92 closed, the sleeve 66 provides a frictional grip of the proximal end 91 of the catheter knob 20.

Referring now to FIGS. 2–4 and 7–8, the catheter knob 20 has a proximal bore 90 that can be sleeved over the second extension 72 in a manner such that the outer surface of the catheter knob 20 can be substantially flush with the outer surface of the first extension 70 (as best shown in FIGS. 3 and 4). The proximal bore 90 houses the sonic connector 36 and a nesting piece 94. An elastic element 96, such as a spring, is seated in the distal part of the proximal bore 90, and has one end carried on a projection 98 provided at the distal end of the nesting piece 94. The nesting piece 94 has a generally cylindrical configuration and has a receptacle 100 which functions to selectively retain the sonic connector 36, as will be explained in greater detail below. In addition, a control ring 110 is positioned around the outer surface 112 of the catheter knob 20. The control ring 112 cooperates with the nesting piece 94 to move the nesting piece 94 in a reciprocal manner inside the proximal bore 90 of the catheter knob 20, as explained below.

Figure 7:
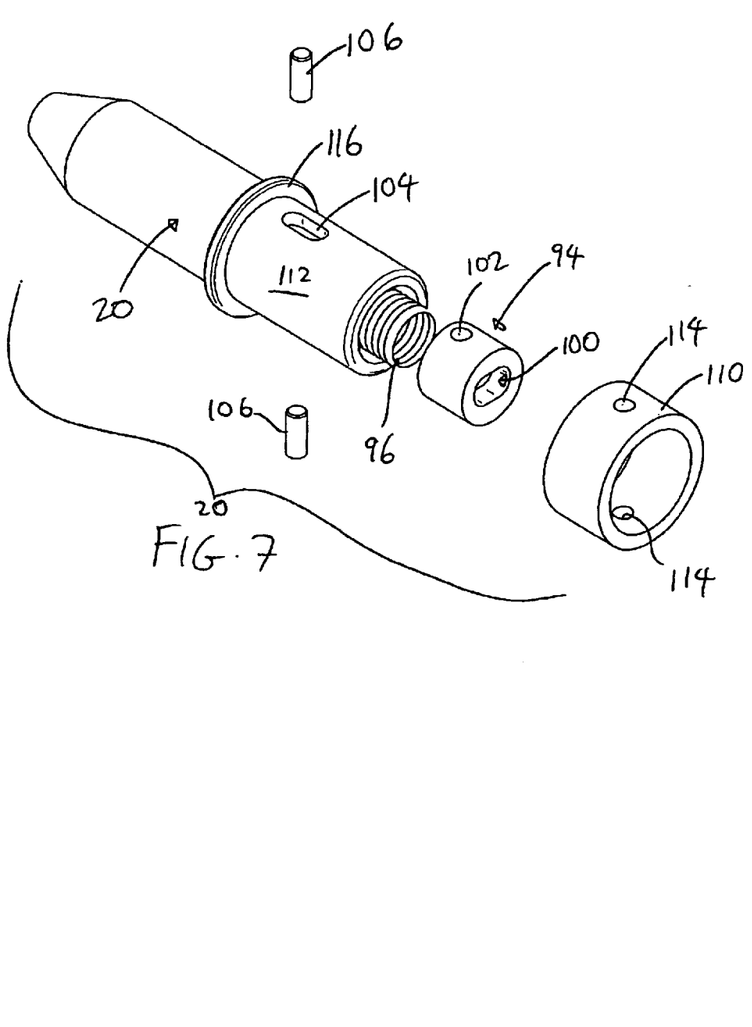
FIG. 7 is an exploded perspective view of the catheter knob of the system of FIG. 1.
Figure 8:
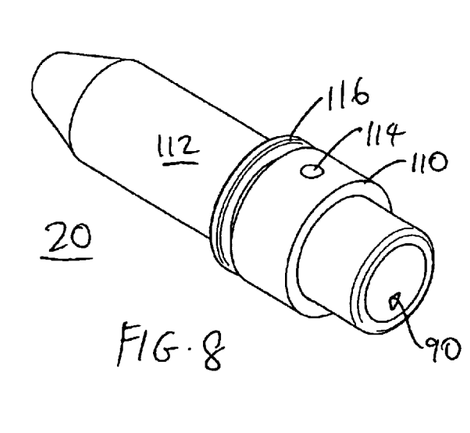
FIG. 8 is an assembled perspective view of the catheter knob of FIG. 7.

The nesting piece 94 has two opposite and aligned openings 102; only the top opening 102 is shown in FIG. 7, but the bottom opening is the same and is aligned on a straight line with the top opening 102. Similarly, the catheter knob 20 has two opposite and aligned channels 104; only the top channel 104 is shown in FIG. 7, but the bottom channel is the same and is aligned on a straight line with the top channel 104. In addition, the control ring 110 has two opposite and aligned openings 114. The channels 104 and the openings 102, 114 are aligned, as best shown in FIGS. 3 and 4. Two opposing pins 106 are provided, with each pin 106 adapted to be fitted inside a corresponding set of channel 104 and openings 102, 114, so as to couple the control ring 110 and the nesting piece 94 as a unitary moving piece. The width of the channels 104 define the distal and proximal limits of movement for the control ring 110 and the nesting piece 94. The catheter knob 20 also has an annular flange 116 provided about its outer surface 112 that also defines the distal limit of the movement of the control ring 110.

In use, the sonic connector 36 is shown in FIGS. 3–4 as connecting the transducer horn 42 (e.g., with a threaded connection) with the ultrasound transmission member 32. The sonic connector 36 is always located at a fixed position inside the proximal bore 90 of the catheter knob 20. When the slide collar assembly 22 is in the non-supporting position shown in FIGS. 3, 9 and 11, the elastic element 96 normally biases the nesting piece 94 in the proximal direction so that the sonic connector 36 is received inside the receptacle 100 of the nesting piece 94 to be supported by the nesting piece 94. The proximal movement of the nesting piece 94 will cause the pins 106 to move in the proximal direction inside the channels 104, thereby causing the control ring 110 to move proximally away from the flange 116. The outer ring 52 and the inner ring 50 are positioned completely over the proximal section 80 of the sleeve 66, with the narrowed proximal end 57 positioned adjacent the cylindrical wall 68 of the transducer housing 24.

Figures 9, 10:
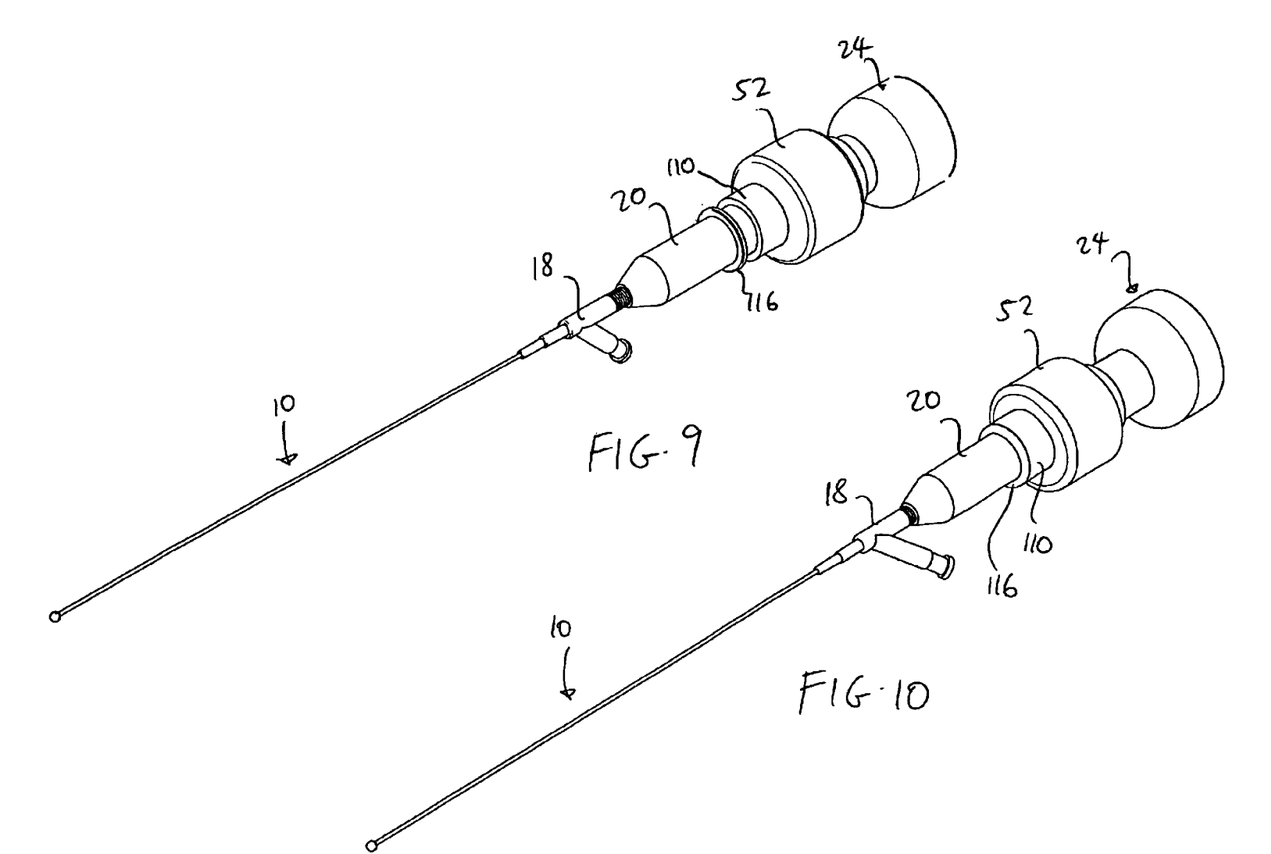
FIG. 9 is a perspective view of the system of FIG. 1 with the slide collar assembly in the non-supporting position.
FIG. 10 is a perspective view of the system of FIG. 1 with the slide collar assembly in the supporting position.
Figures 11, 12:
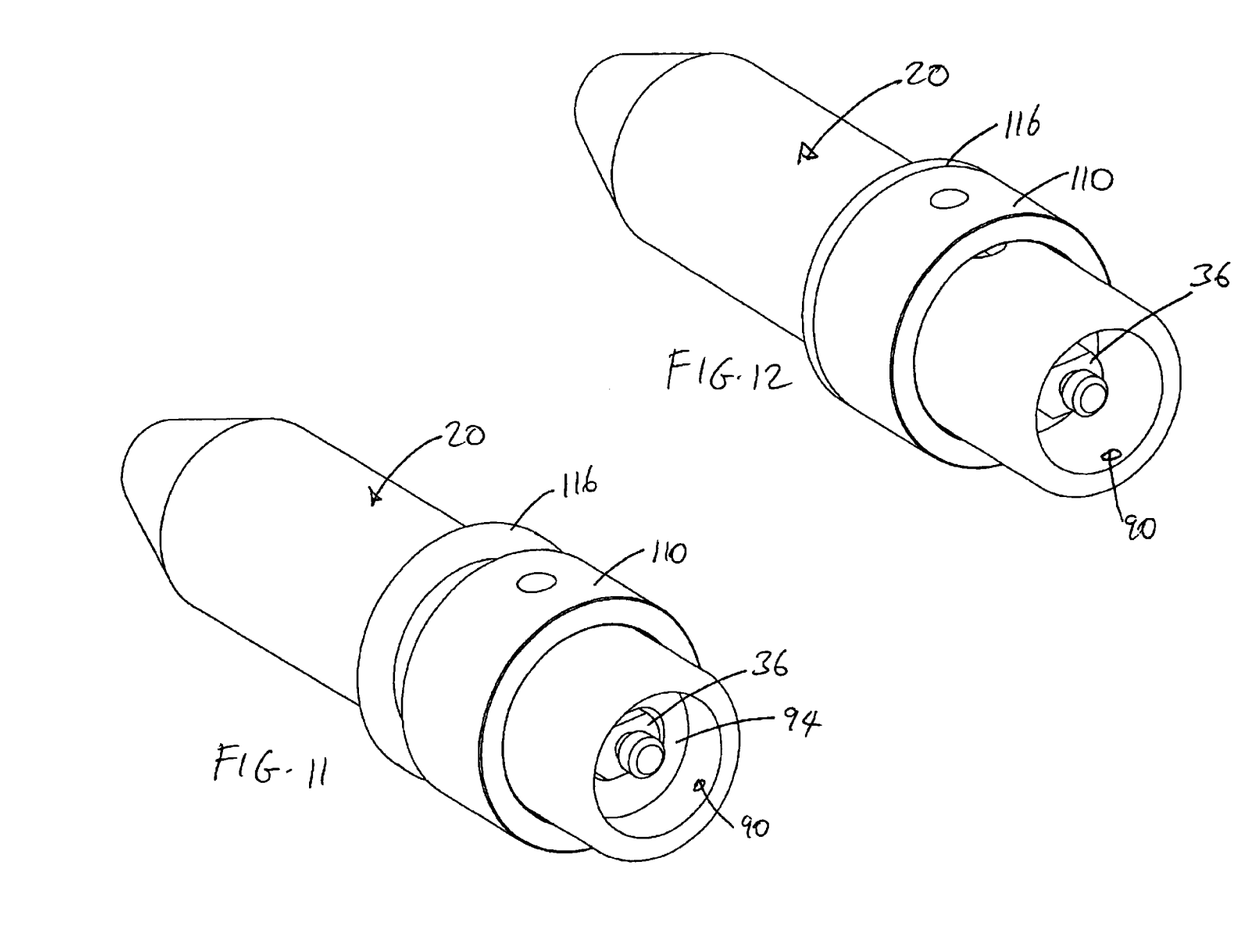
FIG. 11 is a perspective view of the catheter knob of the system of FIG. 1 with the slide collar assembly in the non-supporting position.
FIG. 12 is a perspective view of the catheter knob of the system of FIG. 1 with the slide collar assembly in the supporting position.

When the slide collar assembly 22 is now moved from the non-supporting position to the supporting position shown in FIGS. 4, 10 and 12, the user pushes the outer ring 52 in the distal direction. The step 55 on the distal end of the inner ring 50 engages the proximal end of the control ring 110 and pushes the control ring 110 in the distal direction. Movement of the control ring 110 in the distal direction will cause the pins 106 to move in the distal direction inside the channels 104, thereby causing the nesting piece 94 to counter the bias of the elastic element 96 and move in the distal direction. As the nesting piece 94 moves in the distal direction, the sonic connector 36 becomes free from the receptacle 100 of the nesting bore 94. In addition, the distal movement of the inner ring 50 will cause the inner surface of the inner ring 50 to engage the enlarged distal section 82 of the sleeve 66, which functions to close the slot 92 so as to frictionally grip the proximal portion 91 of the knob 20 when the slide collar assembly 22 is in the supporting position. The flange 116 and the width of the channels 104 function as stops to limit the distal movement of the control ring 110.

In the supporting position, the sonic connector 36 is not supported by the nesting piece 94 so that the sonic connector 36 can be free from any component or material interfaces, thereby promoting improved ultrasound energy propagation. The medical procedure can then be carried out while the slide collar assembly 22 is in the supporting position. Upon completion of the medical procedure, the above-described steps are reversed. In particular, the combined inner and outer rings 50, 52 (slide collar assembly 22) are retracted in the proximal direction so that they are now positioned over the proximal section 80 of the sleeve 66. The bias of the elastic element 96 will push the nesting piece 94 in the proximal direction so that the sonic connector 36 is received inside the receptacle 100 of the nesting piece 94. In addition, the proximal movement of the nesting piece 94 will cause the pins 106 to move in the proximal direction inside the channels 104, thereby causing the control ring 110 to move proximally away from the flange 116. Now, the catheter 10 can be disconnected from the transducer 34.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound system, comprising:
    an ultrasound transducer having a transducer housing having a distal end, and a horn provided at the distal end of the transducer housing;
    an ultrasound transmission member having a proximal end;
    a sonic connector that is connected to the horn and the proximal end of the ultrasound transmission member;

a catheter knob having a proximal end that is coupled to the distal end of the transducer housing, the catheter knob having a proximal bore that houses the sonic connector; and a nesting piece that is retained inside the proximal bore of the catheter knob, the nesting piece movable from a first position where the sonic connector is received inside the nesting piece to a second position where the sonic connector is separated from the nesting piece when ultrasound energy is being propagated through the ultrasound transmission member.

2. The system of claim 1, further including:

means for biasing the nesting piece from the second position to the first position; and means for moving the nesting piece from the first position to the second position.

3. The system of claim 1, further including:

an elastic element retained inside the proximal bore of the catheter knob for biasing the nesting piece from the second position to the first position; and a control ring that is operatively coupled to the nesting piece for moving the nesting piece from the first position to the second position.

4. The system of claim 3, further including:

a collar movably positioned over the distal end of the transducer housing and movable from a first position where the collar is spaced apart from the control ring to a second position where the collar engages and pushes the control ring.

5. The system of claim 4, further including means for maintaining the collar in the second position.

6. The system of claim 4, wherein the collar has an inner ring that has a bore, and an outer ring that has a bore, with the inner ring received inside the bore of the outer ring.

7. The system of claim 6, wherein the proximal end of the catheter knob is partially positioned inside the bore of the inner ring when the inner ring is in the second position.

8. The system of claim 6, further including a sleeve partially retained inside the bore of the inner ring, the sleeve having a longitudinal slot, and wherein each of the inner ring and the outer ring has an opening, with a pin extending through the opening in the inner ring and the opening in the outer ring.

9. The system of claim 8, wherein the slot is opened when the nesting piece is in the first position, and the slot is closed when the nesting piece is in the second position.

10. The system of claim 9, wherein the sleeve grips the catheter knob when the slot is closed.

11. The system of claim 3, wherein the catheter knob has a longitudinal channel, and wherein each of the nesting piece and the control ring has an opening, with a pin extending through the opening in the nesting piece and the opening in the control ring, and traveling within the channel.

12. A method of using an ultrasound system during a medical procedure, comprising:

a. providing an ultrasound system having:

an ultrasound transducer having a transducer housing having a distal end, and a horn provided at the distal end of the transducer housing;

an ultrasound transmission member having a proximal end;

a sonic connector that is connected to the horn and the proximal end of the ultrasound transmission member;

a catheter knob having a proximal end that is coupled to the distal end of the transducer housing, the catheter knob having a proximal bore that houses the sonic connector; and a nesting piece that is retained inside the proximal bore of the catheter knob;

b. moving the nesting piece from a first position where the sonic connector is received inside the nesting piece to a second position where the sonic connector is separated from the nesting piece when ultrasound energy is being propagated through the ultrasound transmission member.

13. An ultrasound system, comprising:

an ultrasound transducer;

an ultrasound transmission member having a proximal end;

a sonic connector that is connected to the ultrasound transducer and the proximal end of the ultrasound transmission member; and a nesting piece that is movable from a first position where the sonic connector is received inside the nesting piece to a second position where the sonic connector is separated from the nesting piece when ultrasound energy is being propagated through the ultrasound transmission member.

14. The system of claim 13, wherein the ultrasound transducer has a transducer housing having a distal end, and a horn provided at the distal end of the transducer housing, with the sonic connector connected to the horn.

15. The system of claim 13, further including a catheter knob having a proximal bore that houses the sonic connector and the nesting piece.

16. The system of claim 15, further including:

an elastic element retained inside the proximal bore of the catheter knob for biasing the nesting piece from the second position to the first position; and a control ring that is operatively coupled to the nesting piece for moving the nesting piece from the first position to the second position.

17. The system of claim 16, further including:

a collar movably positioned over the transducer and movable from a first position where the collar is spaced apart from the control ring to a second position where the collar engages and pushes the control ring.

18. The system of claim 17, further including means for maintaining the collar in the second position.

19. The system of claim 17, wherein the collar has an inner ring that has a bore, and an outer ring that has a bore, with the inner ring received inside the bore of the outer ring.

20. The system of claim 13, further including:

means for biasing the nesting piece from the second position to the first position; and means for moving the nesting piece from the first position to the second position.

* * * * *